US010105057B2

(12) United States Patent
Hendriks et al.

(10) Patent No.: US 10,105,057 B2
(45) Date of Patent: Oct. 23, 2018

(54) APPARATUS FOR OPTICAL ANALYSIS OF AN ASSOCIATED TISSUE

(75) Inventors: Bernardus Hendrikus Wilhelmus Hendriks, Eindhoven (NL); Rami Nachabe, Eindhoven (NL); Gerhardus Wilhelmus Lucassen, Eindhoven (NL); Adrien Emmanuel Desjardins, Waterloo (CA); Theodoor Jacques Marie Ruers, Zeist (NL)

(73) Assignee: Koninklijke Philips N.V., Eindhoven (NL)

( * ) Notice: Subject to any disclaimer, the term of this patent is extended or adjusted under 35 U.S.C. 154(b) by 1137 days.

(21) Appl. No.: 13/995,967

(22) PCT Filed: Dec. 22, 2011

(86) PCT No.: PCT/IB2011/055885
§ 371 (c)(1),
(2), (4) Date: Jun. 20, 2013

(87) PCT Pub. No.: WO2012/093309
PCT Pub. Date: Jul. 12, 2012

(65) Prior Publication Data
US 2014/0200459 A1 Jul. 17, 2014

(30) Foreign Application Priority Data
Jan. 4, 2011 (EP) .................................... 11150095

(51) Int. Cl.
*A61B 6/00* (2006.01)
*A61B 5/00* (2006.01)
(Continued)

(52) U.S. Cl.
CPC .............. *A61B 5/0075* (2013.01); *A61B 1/00* (2013.01); *A61B 5/0084* (2013.01);
(Continued)

(58) Field of Classification Search
USPC ......................................... 600/407, 473, 476
See application file for complete search history.

(56) References Cited

U.S. PATENT DOCUMENTS 5,769,791 A * 6/1998 Benaron et al. .............. 600/473
5,939,327 A 8/1999 Samsoondar
(Continued)

FOREIGN PATENT DOCUMENTS

JP H03114441 A 5/1991
JP H07149632 A 6/1995
(Continued)

OTHER PUBLICATIONS

Kommera, Sarita. "Spectroscopic Characterization of Biliary Tract Tissue In-Vivo to Assist Lapartoscopic Cholecsytectomy." Dec. 2006. University of Texas at Arrlington. pp. 1-88 (plus 12 pages of preface).*
(Continued)

*Primary Examiner* — James Kish

(57) ABSTRACT

The present invention relates to an apparatus 100 and, a method and a computer program for determining a parameter indicative of a tissue type of an associated tissue 116. In particular, the invention relates to an apparatus 100 comprising a spectrometer 102, which spectrometer comprises a light source 104 and a detector 106, 108 arranged to measure an optical spectrum. This enables determination of a first parameter being indicative of a bile concentration. As the inventors of the present invention have made the insight that bile concentration may serve as a discriminative feature for different tissue types, the apparatus is arranged to determine a second parameter indicative of a tissue type based on a concentration of bile. According to a specific embodiment, the apparatus further comprises an interventional device 112.

15 Claims, 7 Drawing Sheets

(51) Int. Cl.
 *A61B 1/00* (2006.01)
 *G01N 21/25* (2006.01)
 *A61B 18/18* (2006.01)

(52) U.S. Cl.
 CPC ............ *A61B 5/4836* (2013.01); *A61B 18/18* (2013.01); *G01N 21/25* (2013.01)

(56) References Cited

U.S. PATENT DOCUMENTS

| | | | |
|---|---|---|---|
| 6,405,074 | B1 | 6/2002 | Banerjee |
| 6,526,299 | B2 | 2/2003 | Pickard |
| 7,167,736 | B2 | 1/2007 | Winther |
| 7,419,483 | B2 | 9/2008 | Shehada |
| 7,753,902 | B1 | 7/2010 | Mansour et al. |
| 2004/0162489 | A1 | 8/2004 | Richards-Kortum et al. |
| 2006/0035827 | A1* | 2/2006 | Green ............................ 514/12 |
| 2006/0200012 | A1 | 9/2006 | Mansour et al. |
| 2006/0241347 | A1 | 10/2006 | Whitehead |
| 2008/0306337 | A1 | 12/2008 | Livingston et al. |
| 2009/0046286 | A1* | 2/2009 | Masilamani et al. ......... 356/317 |
| 2010/0056928 | A1 | 3/2010 | Zuzak et al. |
| 2010/0160791 | A1 | 6/2010 | Liu et al. |
| 2010/0173350 | A1 | 7/2010 | Masilamani et al. |

FOREIGN PATENT DOCUMENTS

| | | | | |
|---|---|---|---|---|
| JP | 01221136 | A | 8/2001 | |
| JP | 2006205640 | A | 8/2006 | |
| JP | 2007149632 | A | 6/2007 | |
| JP | 2010258022 | A | 11/2010 | |
| SU | 1617375 | | 12/1990 | |
| WO | WO2004090500 | | 10/2004 | |
| WO | WO2009153719 | | 12/2009 | |
| WO | WO2010/086859 | * | 8/2010 | ............ G01N 33/48 |

OTHER PUBLICATIONS

F. Baldini et al., "Analysis of the Optical Properties of Bile", Journal of Biomedical Optics Jul. 2000, vol. 5, No. 3, pp. 321-329.

T. Farrell et al., "A Diffusion Theory model of Spatially Resolved, Steady-State Diffuse Reflectance for the Noninventive Determination of Tissue Optical Properties in vivo", Med. Phys. 19 (4), Jul./Aug. 1992, pp. 879-888.

E.H. Livingston et al., "In Vivo Spectroscopic Characterization of Porcine Biliary Tract Tissues: First Step in the Development of New Biliary Tract Imaging Devices", Annals of Biomedical Engineering, vol. 17, No. 1, Jan. 2009, pp. 201-209.

D.J. Maitland et al., "Optical properties of Human Gallbladder Tissue and Bile", Applied Optics, vol. 32, No. 4, Feb. 1, 1993, pp. 586-591.

S. McGee et al., "Model-Based Spectroscopic Analysis of the Oral Cavity: Impact of Anatomy", Journal of Biomedical Optics, Nov./Dec. 2008, vol. 13(6), pp. 064034-1-064034-15.

R. Nachabe et al., "Estimation of Lipid and Water Concentrations in Scattering media with Diffuse Optical Spectroscopy from 900 to 1600 nm", Journal of Biomedical Optics 15(3), May/Jun. 2010, pp. 037015-1-037015-10.

R. Nachabe et al., "Estimation of Biological Chromophores Using Diffuse Optical Spectroscopy: Benefit of Extending the UV-VIS Wavelength Range to Include 1000 to 1600 nm", Optics Express, Nov. 22, 2010, vol. 18, No. 24, pp. 1432-1442.

N. Rajaram et al., "Lookup Table-Based Inverse model for Determining Optical Properties of Turbid Media", Journal of Biomedical Optics, Sep./Oct. 2008, vol. 13(5), pp. 050501-1-050501-3.

Nagana, G. et al. "Visualization of Bile Homeostasis Using 1H-NMR Spectroscopy as a Route for Assessing Liver Cancer", Lipids, vol. 44, No. 1, Jan. 31, 2009, pp. 27-35.

* cited by examiner

APPARATUS FOR OPTICAL ANALYSIS OF AN ASSOCIATED TISSUE

FIELD OF THE INVENTION

The present invention relates to an apparatus for optical analysis of an associated tissue, and more specifically to an apparatus, a method and a computer program for determination of a parameter indicative of tissue type of the associated tissue.

BACKGROUND OF THE INVENTION

During interventions in the field of surgical oncology and liver cancer treatment including associated structures, it is important to be able to discriminate pathological tissue from normal tissue in order for instance to ensure that the treatment is performed on the correct location. Also in the case of surgery, for instance during cholecystectomies, discriminating bile ducts from artery and veins is important to guide the surgery. Although differences in blood content will likely provide possibilities to discriminate certain structures of the liver organ, they are not always sufficient for instance in early stage liver cancer. An apparatus which could aid in discriminating certain structures of the liver organ would be advantageous.

U.S. Pat. No. 7,419,483 discloses a surgical drain having at least one sensor for monitoring and/or recording the condition of an anatomical site or fluid emitted from the site where the surgical drain is placed. The system may also include modifications of the surgical drain to improve stabilization or immobilization in the proximity of the anatomical site to be monitored. The system may be rather complicated, since it includes modifications of the surgical drain to improve stabilization or immobilization in the proximity of the anatomical site to be monitored.

Hence, an improved apparatus for determination of a parameter indicative of tissue type of the associated tissue would be advantageous, and in particular a more simple and reliable apparatus would be advantageous.

SUMMARY OF THE INVENTION

In particular, it may be seen as an object of the present invention to provide an apparatus, a method and a computer program for determination of a parameter indicative of tissue type of the associated tissue that solves the above mentioned problems of the prior art with being simple, effective and versatile.

It is a further object of the present invention to provide an alternative to the prior art.

Thus, the above described object and several other objects are intended to be obtained in a first aspect of the invention by providing an apparatus for optical analysis of an associated tissue, the apparatus comprising:

a spectrometer for obtaining measured data representative of an optical spectrum of the associated tissue, the spectrometer comprising
  a light source, and
  an optical detector, and
  a processor arranged for
    receiving the measured data,
    determining from the measured data a first parameter being indicative of a concentration of bile in said associated tissue, and
    determining from the first parameter a second parameter being indicative of a tissue type.

The invention is particularly, but not exclusively, advantageous for obtaining a simple and reliable apparatus for optical analysis of an associated tissue. The apparatus may be seen as simple in that it enables procurement of measured data representative of an optical spectrum, and furthermore enables extraction of information from the measured data for assigning a parameter to the associated tissue. The invention is based on the insight made by the present inventors that a concentration of bile in an associated tissue may serve as a discriminative feature, such as for discriminating between tissue types. When referring to discrimination between tissue types, it is understood to that such discrimination may include discrimination between tissue structures, such as discrimination between the bile duct, blood vessels and the surrounding tissue. This may be relevant in order to prevent bile duct injuries during cholecystectomies. It is further understood that such discrimination may include discrimination between tissue conditions, such as discrimination between dysplastic tissue and normal tissue, such as discrimination between normal tissue and tumor tissue. This may be relevant in order to ensure that the treatments in the field of oncology are performed on the correct location. For instance ablation of a small tumor lesion in the liver requires accurate placement of the ablation needle tip. Image guidance by for instance X-ray or ultrasound can provide valuable feedback but these means of navigation do not provide real time tissue feedback from the tip of the needle. This makes targeting small lesions difficult with these techniques. Another advantage of the invention may be that it enables more reliable discrimination between tissue types, since it enables the determination and use of a new discriminative feature, namely the concentration of bile. The invention provides a technical solution to a technical problem, and may assist a physician in reaching a diagnosis or treating a patient.

Bile is understood to be pure human bile. When referring to concentration of bile, it is understood that the concentration of bile is to be measured relative to pure human bile. In other words, pure human bile is our reference. Hence 100 vol % bile means pure human bile. In a specific embodiment, bile is measured in volume percentage (vol %). In one embodiment, bile is understood to be pure human bile, and the optical properties of such pure human bile are measured on one or more samples of human bile. In one other embodiment, bile is understood to be pure human bile, and the optical properties of such pure human bile is determined from knowledge in the art regarding bile, such as can be obtained, for example from the reference "Analysis of the optical properties of bile", Francesco Baldini, Paolo Bechi, Fabio Cianchi, Alida Falai, Claudia Fiorillo, Paolo Nassi in Journal of Biomedical Optics 5(3), 321-329 (July 2000), which is hereby incorporated by reference in its entirety.

Light is to be broadly construed as electromagnetic radiation comprising wavelength intervals including visible, ultraviolet (UV), near infrared (NIR), infra red (IR), x-ray. The term optical is to be understood as relating to light.

An optical spectrum is understood to be information related to a plurality of wavelengths of light, such as an intensity parameter, an absorption parameter, a scattering parameter or a transmission parameter given for a plurality of wavelengths of light. A continuous spectrum represents spectral information, but it is further understood, that information related to light at discrete wavelengths may represents an optical spectrum.

A spectrometer is understood as is common in the art. It is understood, that the spectrometer comprises means for selecting wavelengths, such as transmission filters or gratings. Alternatively, wavelength specific light sources, such as light emitting diodes or LASERs, may be used or wavelength specific optical detectors may be used. A spectral filtration may occur at different places in the system, for instance it may occur between the second light source and the interventional device, it may occur in the interventional device, or it may occur between the interventional device and the optical detector.

An interventional device is generally known in the art, and may include any one of an endoscope, a catheter, a biopsy needle.

The invention can be used in the field of oncology, or other healthcare applications where the determination of tissue type is relevant.

The apparatus may be applicable for real-time intra-operative needle localization and ablation monitoring to improve ablation efficacy and disease free survival.

In an embodiment of the invention, there is provided an apparatus for optical analysis of an associated tissue wherein the processor is further arranged for determining a scattering parameter based on the measured data. A possible advantage of this may be that determination of a scattering parameter renders it possible to take the scattering parameter into account. For example, an algorithm for disentangling contributions from different optically active constituents, such as chromophores, in a sample may not be able to correctly disentangle the contributions and correctly quantify the constituents if scattering is present in the sample, unless the algorithm determines the scattering parameter and takes it into account.

In an embodiment of the invention, there is provided an apparatus for optical analysis of an associated tissue the apparatus further comprising an interventional device, the interventional device comprising a first guide for guiding photons from the light source to an exit position on a distal end of the interventional device, the photons being emittable from the exit position, and a second guide for guiding photons from an entry position on the distal end of the interventional device and to the optical detector.

In one embodiment, the first guide and the second guide may be one and the same guide. In another embodiment, the first guide and the second guide may be two separate guides which are spatially distanced from each other. The first and second are understood to be light guides, such as optical fibers, such as optical waveguides.

In an embodiment of the invention, there is provided an apparatus for optical analysis of an associated tissue, wherein the exit position and the entry position are spatially separated and spatially oriented so that, upon positioning the distal end of the interventional device adjacent to the associated tissue, an average spectral information of a region of the associated tissue is obtainable from photons collectable at the entry position. An advantage of this is that photons emitted at the exit position and collected at the entry position may have traveled a distance outside of the interventional device, such as in the associated tissue.

In an embodiment of the invention, there is provided an apparatus further comprising any one of: a light source for providing therapeutic light and/or an ultrasound unit. A possible advantage of providing a therapeutic light source is that it enables therapy using light. An advantage of providing an ultrasound unit may be that it enables ablation, such as radio frequency ablation or imaging.

In an embodiment of the invention, there is provided an apparatus wherein the photons exiting the exit position are non-focused. A possible advantage of this is that the energy is divided over a broader area of the associated tissue due to the defocusing, and as a result there is less risk of damaging the adjacent sample.

In an embodiment of the invention, there is provided an apparatus wherein the apparatus further comprises a database, which database is operably connected to the processor. An advantage of this may be, that the processor may access data stored in the database, which data may be beneficial for determining from the data measured data a first parameter being indicative of a concentration of bile in said associated tissue, and determining from the first parameter a second parameter being indicative of a tissue type.

In a further embodiment of the invention, there is provided an apparatus wherein the database comprises predetermined data representative of an optical spectrum. Having predetermined data representative of an optical spectrum stored in the database may be beneficial for determining from the measured data a first parameter being indicative of a concentration of bile in said associated tissue, and determining from the first parameter a second parameter being indicative of a tissue type. The predetermined data may be representative of spectra of a tissue type, or the predetermined data may be representative of an optical spectrum of a chromophore expected to be in the associated tissue, which may be useful, e.g., as an input parameter in a mathematical model.

In a further embodiment of the invention, there is provided an apparatus wherein the predetermined data is representative of an optical spectrum of human bile. This may be beneficial, e.g., for disentangling the contributions to the measured data from different chromophores. This may also be beneficial for enabling determination of a quantitative estimate of a concentration of bile in the associated tissue.

According to a second aspect of the invention, the invention further relates to a method for optical analysis of an associated tissue, the method comprising the steps of:

receipt of data representative of an optical spectrum of the associated tissue, determination of a first parameter, the first parameter being indicative of a concentration of bile, based on the measured data, and determination of a second parameter based on the first parameter, the second parameter being indicative of a tissue type.

The method does not require interaction with a patient's body or involvement of a medical practitioner.

In one embodiment a method for optical analysis of an associated tissue is provided, wherein the determination of the first parameter includes fitting the measured data to a mathematical model. A mathematical model is in the present context understood to be a theoretical expression which for a given set of input parameters having influence on the optical spectrum, for example quantities of chromophores present and amount of scattering may as output yields data representative of an optical spectrum. Fitting is understood to be the process of adjusting the input parameters so as minimize a difference between a measured optical spectrum and a theoretically given optical spectrum. An advantage of fitting is that fitting may be used to quantitatively estimate the input parameters.

In one embodiment a method for optical analysis of an associated tissue is provided, wherein the determination of the first parameter includes any one of:

assessing a look-up-table comprising predetermined optical spectra, and performing multivariate analysis.

The predetermined optical spectra may include spectra which have been calculated theoretically, such as by mathematical models, or spectra which have been measured on phantoms, such as samples prepared by mixing constituents expected to be in the associated tissue. Multivariate analysis is commonly known in the art and understood to include Principal Components Analysis (PCA) and least squares discriminant analysis.

In one embodiment a method for optical analysis of an associated tissue is provided, the method further including the step of:

determination of a ratio between a concentration of biliverdin and a concentration of bilirubin.

An advantage of this may be that the ratio between a concentration of biliverdin and a concentration of bilirubin may serve as an input in the determination of the second parameter, which may improve the determination of the second parameter in terms of quality of determination, such as accuracy of determination.

In one embodiment a method for optical analysis of an associated tissue is provided, the method further comprising the step of:

determination of a concentration of cholesterol.

In one embodiment, information about optical absorption in the infrared is used to estimate the cholesterol content present in bile. The ratio of bile salts to cholesterol may be correlated with the propensity to develop gall stones, thus estimations of the cholesterol may be valuable in this respect, for instance when conducted in a minimally-invasive manner by a catheter positioned in the bile duct.

According to a third aspect of the invention, the invention further relates to a computer program product being adapted to enable a computer system comprising at least one computer having data storage means associated therewith to operate a processor arranged for carrying out the method according to the second aspect of the invention.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The apparatus, method and a computer program for determination of a parameter indicative of tissue type of the associated tissue according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
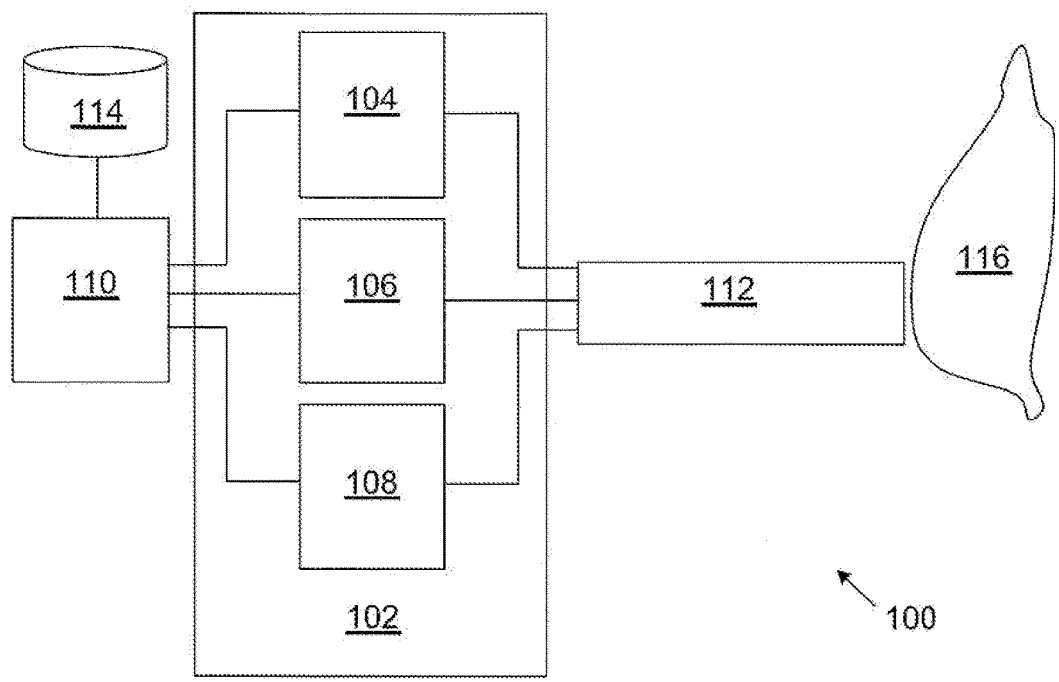
FIG. 1 shows a diagrammatic depiction of an apparatus according to an embodiment of the invention.

FIG. 1 shows a diagrammatic depiction of an apparatus according to an embodiment of the invention comprising a spectrometer 102 comprising a light source 104, a first optical detector 106, a optional second optical detector 108 and an interventional device 112, where the interventional device 112 has one or more guides, such as optical elements, such as optical waveguides, capable of guiding light from the light source 104 to a distal end of the interventional device so as to emit the light at the distal end of the interventional device, and furthermore capable of guiding light back from the distal end of the interventional device to the first optical detector 106 and/or second optical detector 108. The light guides enable light to enter an associated tissue 116, such as a liver tissue, and the light guides further enable light exiting the associated tissue to be collected and led to the optical detector. The apparatus thus enables procurement of measured data representative of an optical spectrum of the associated tissue 116. The optical detectors 106, 108 may be controlled by processor 110 so as to acquire the measured data. The processor may have access to a database 114. In a specific embodiment, the apparatus is further arranged to access the database 114, where the database is comprising information regarding various tissue types, and identify which tissue type or tissue types the sample is most likely to comprise, and wherein the identification is based on the second parameter. An advantage of this is that valuable information regarding the tissue type might be obtained this way.

Figure 2:
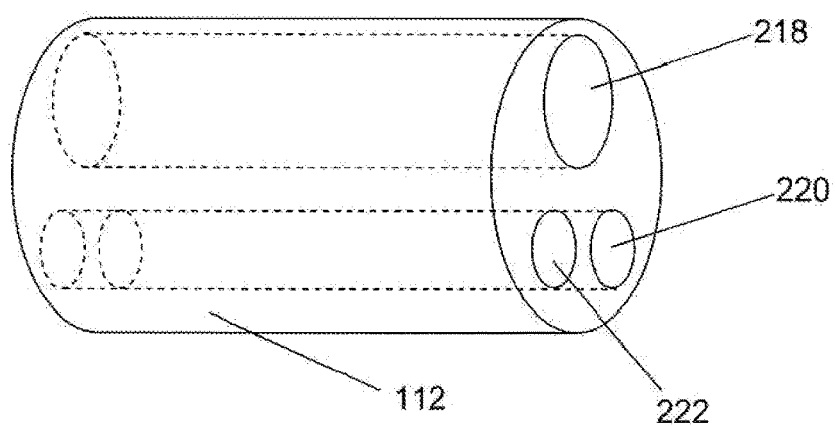
FIG. 2 shows an interventional device according to an embodiment of the invention.

FIG. 2 shows a perspective illustration of an embodiment of an interventional device 112, which interventional device comprises a first guide, a second guide and a third guide. The figure shows an exit position 218 on distal end of the first guide, an entry position 220 on a distal end of the second guide, and an entry position 222 on a distal end of the third guide. The drawing is not to scale. The first, second and third guide are understood to be light guides, such as optical fibers, such as optical waveguides.

In a specific embodiment, the apparatus comprises a light source 104 in the form of a halogen broadband light source with an embedded shutter, an interventional device 112 with three guides and two optical detectors 106, 108 that can resolve light in different wavelength regions, such as substantially in the visible and infrared regions of the wavelength spectrum respectively, such as from 400 nm to 1100 nm and from 800 nm to 1700 nm respectively. The apparatus may furthermore comprise a filter that rejects light for wavelengths below 465 nm which filter may be mounted in front of the optical detectors 106, 108 to reject second order light at the optical detectors. The interventional device 112 has a first guide connected to the light source, the second guide connected to the first optical detector 106 and the third guide connected to the second optical detector 108. The centre-to-centre distance separation between the first (emitting) guide and any one of the second (collecting) guide and the third (collecting) waveguide may be in the millimeter range, such as at least 1 mm, such as at least 2 mm, such as 2.48 mm. All guides may be low-OH fibers of core diameters in the micron range, such as core diameter of 200 microns. Fibers containing low-OH, sometimes also called VIS-NIR fibers, are typically suitable for the visible (VIS) and near infrared (NIR) part of the optical spectrum.

In a particular embodiment, diffuse reflectance spectroscopy is used for obtaining measured data representative of an optical spectrum. Although diffuse reflectance spectroscopy is described to extract tissue properties also other optical methods can be envisioned, such as fluorescence spectroscopy measurements, diffuse optical tomography by employing a plurality of optical fibers, differential path length spectroscopy, or Raman spectroscopy.

The measurement of the optical spectrum can be carried out in various ways, such as by means of various filter systems in different positions of the optical path, one or more light sources emitting in different wavelength bands, or detectors for different wavelength bands. This is understood to be commonly known by the skilled person. It is also possible to modulate the various wavelength bands with different modulation frequencies at the source and demodulate these at the detector, (this technique is described the published patent application WO2009/153719 which is hereby incorporated by reference in its entirety). Various other modifications can be envisioned without departing from the scope of the invention for instance using more than on detector or using more than one light source with different wavelength band, such as Light Emitting Diodes (LEDs) or laser sources.

Figure 3:
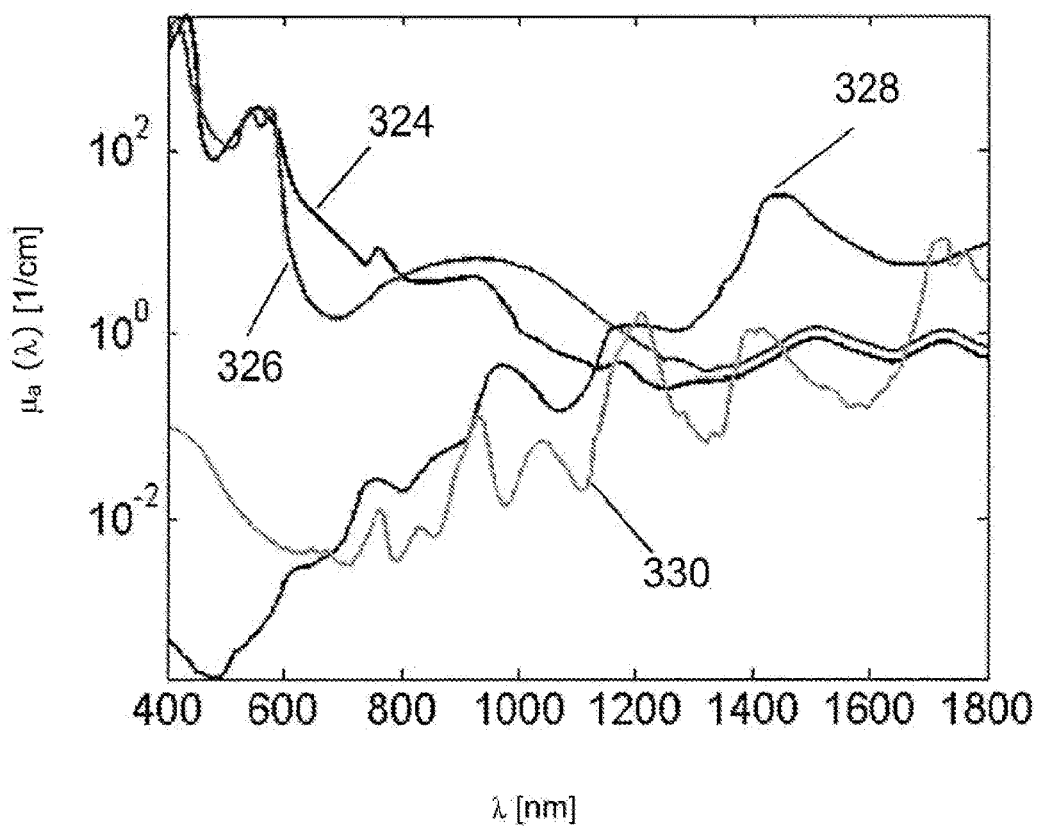
FIG. 3 shows a graph with the absorption coefficient of the chromophores from oxygenated haemoglobin (Hb), deoxygenated haemoglobin (HbO2), water and lipid as a function of the wavelength.

FIG. 3 shows a graph with the absorption coefficient of the chromophores from deoxygenated haemoglobin (Hb) 324, oxygenated haemoglobin (HbO2) 326, water 328 and lipid 330 as a function of the wavelength. Note that blood dominates the absorption in the visible range, while water and lipids dominate in the near infrared range. When a bile containing structure is present the spectra will as well be influenced by bile. The graph has on its first, horizontal axis, the wavelength (λ, lambda) given in nanometer (nm), and on its second, vertical axis, the absorption coefficient $\mu_a$ (mu_a) given in reciprocal centimeters (1/cm).

Figure 4:
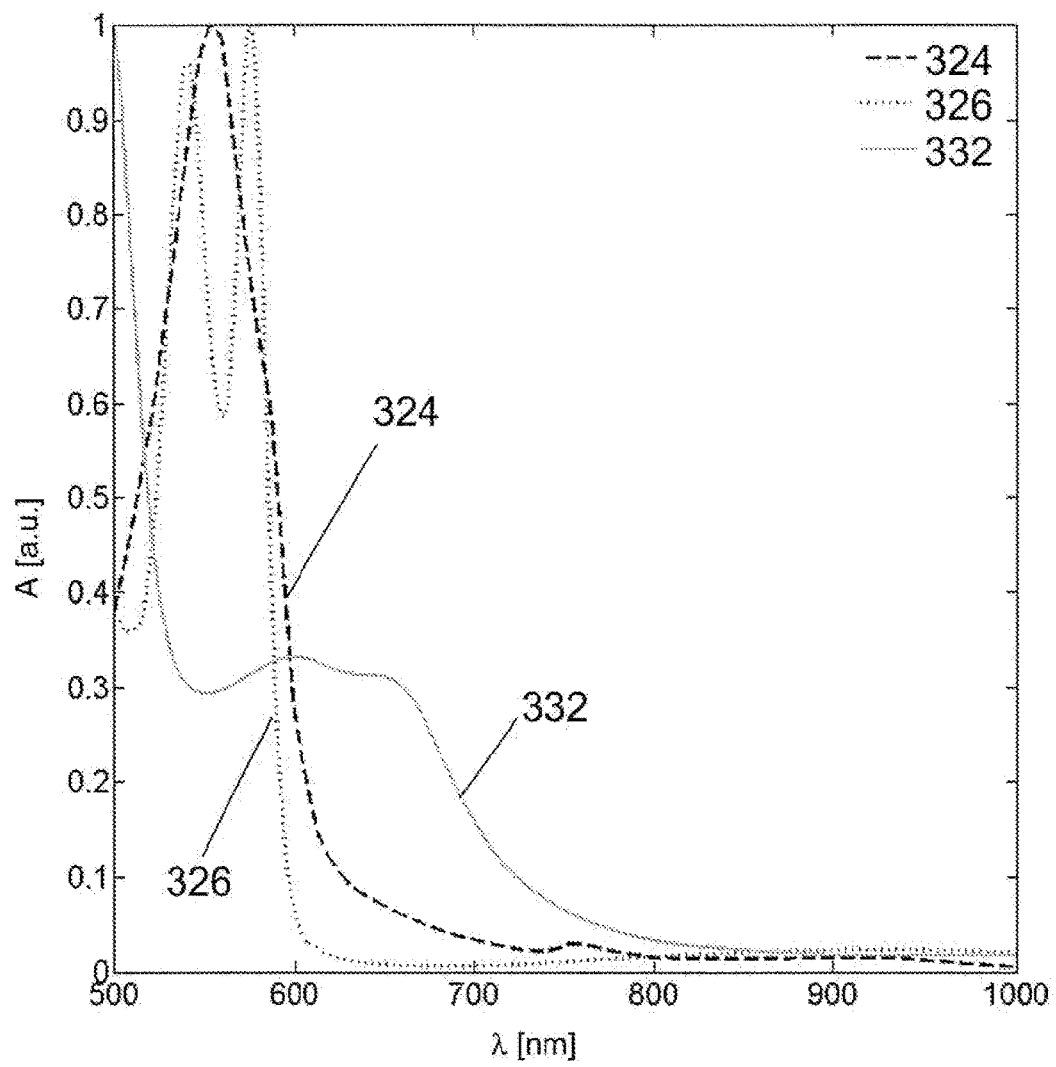
FIG. 4 shows spectra of the absorption coefficient of bile, oxygenated haemoglobin (Hb) and deoxygenated haemoglobin (HbO2)

FIG. 4 shows a graph with spectra of the absorption coefficient of bile 332, deoxygenated haemoglobin (Hb) 324 and oxygenated haemoglobin (HbO2) 326. Bile 332 has a local absorption maximum at 600 nm and another local maximum below 500 nm. The shown spectrum of bile 326 has been measured by the present inventors. The graph has on its first, horizontal axis, the wavelength (λ, lambda) given in nanometer (nm), and on its second, vertical axis, the normalized absorption (A) given in arbitrary units (a.u.). As shown in FIG. 4, given the fact that deoxygenated haemoglobin has higher absorption than oxygenated haemoglobin between 550 and 700 nm where the main absorption of bile is, the fit model without bile compensates for the residual with added deoxygenated haemoglobin leading to higher blood volumes. Hence the observed 758 nm absorption peak of deoxygenated haemoglobin present in the fit and not in the measurement curve in FIG. 5 where no bile is taken into account in the model. To some extent, the Mie slope and Mie-to-Rayleigh fractions also changes whereas the reduced scattering amplitude remains unchanged.

Figure 5:
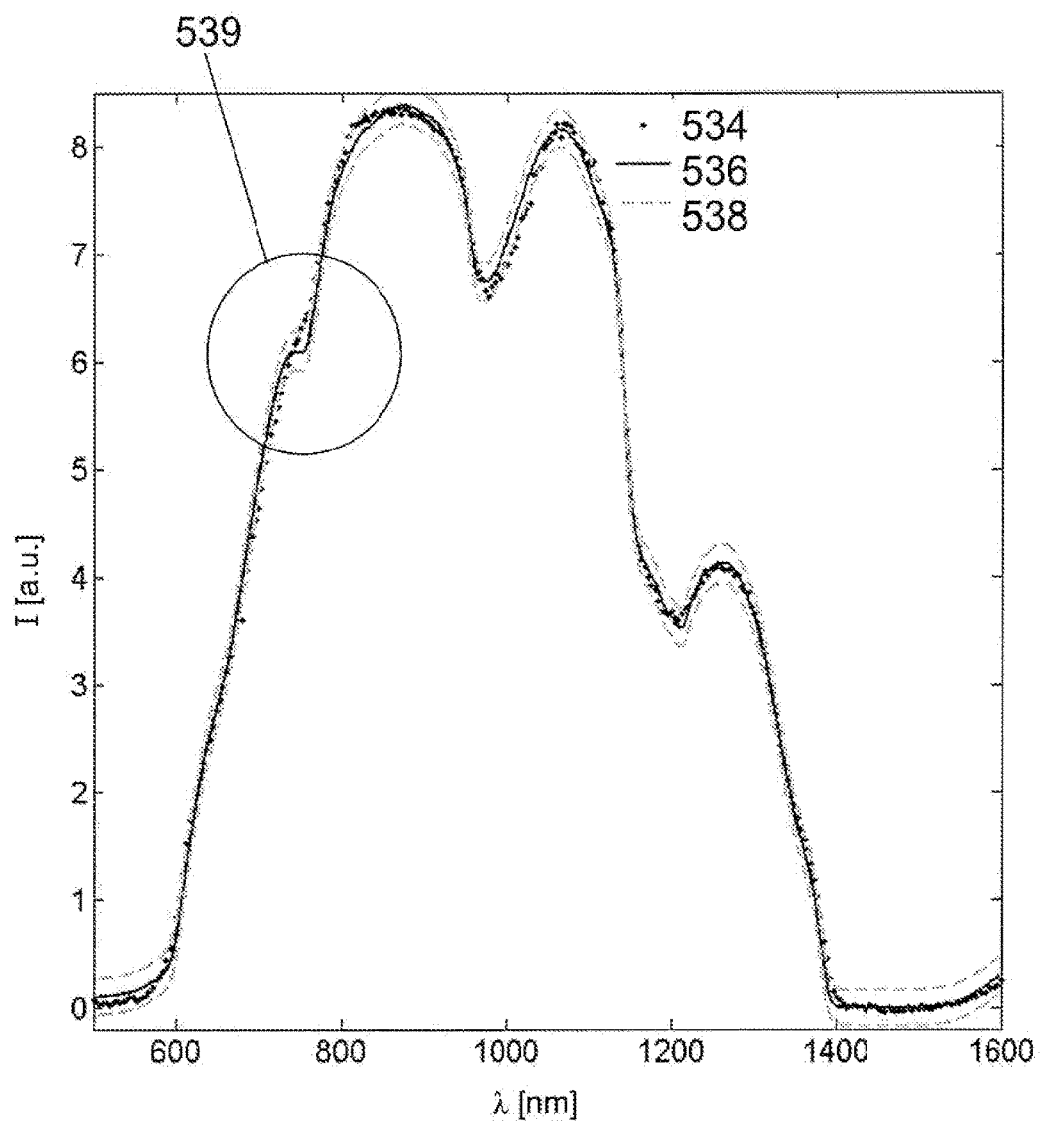
FIG. 5 shows reflectance measurement from a normal ex vivo tissue and corresponding fit with bile in the model.
Figure 6:
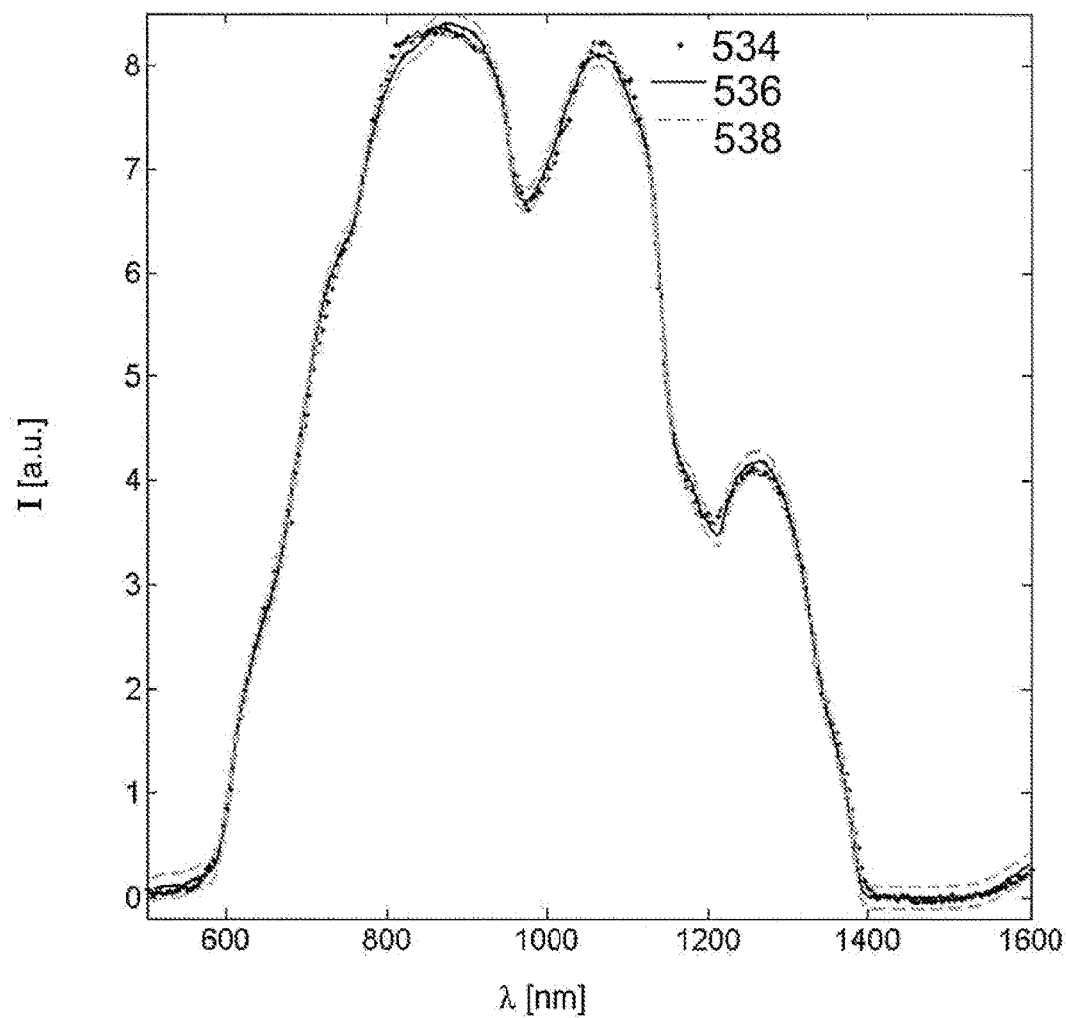
FIG. 6 shows reflectance measurement from a metastatic ex vivo tissue and a fit with bile in the model.

FIG. 5 shows a graph with a reflectance measurement (dotted curve) 534 from a normal ex vivo liver tissue and its fit (full line curve) 536 without bile in the model, and the corresponding 95% confidence bound 538. The graph has on its first, horizontal axis, the wavelength (λ, lambda) given in nanometer (nm), and on its second, vertical axis, the intensity (I) given in arbitrary units (a.u.). From a detailed analysis performed by the present inventors, it has been found that blood cannot account for all the features in the measured spectrum of the liver. As a result it has been found that there is a missing chromophore that has thus far not been accounted for. FIG. 5 shows that when incorporating blood only, deoxyhaemoglobin is overestimated as can be induced from the distinct feature in deoxyhaemoglobin near 758 nm denoted by the dashed circle 539. This feature is presented in the fitted spectrum while in the real measured spectrum this is not present. The inventors of the present invention have made the insight that this difference is caused by the absorption of bile. FIG. 6 shows a graph with a reflectance measurement (dotted curve) 534 from a metastatic ex vivo liver tissue and its fit (full line curve) 536 with bile in the model, and the corresponding 95% confidence bound 538. The graph has on its first, horizontal axis, the wavelength (λ, lambda) given in nanometer (nm), and on its second, vertical axis, the intensity (I) given in arbitrary units (a.u.). In FIG. 4 the absorption coefficient from human bile is shown, revealing a strong absorption near 650 nm compared to haemoglobin of blood. Comparing fitted result (method of fitting a spectra is described in the reference R. Nachabé, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015, 2010, which reference is hereby incorporated by reference, and which reference is hereafter referred to as Nachabé2010) described without and with bile taken into account clearly demonstrates that by taking bile into account the agreement between the fit result and measured spectrum improves significantly.

Figure 7:
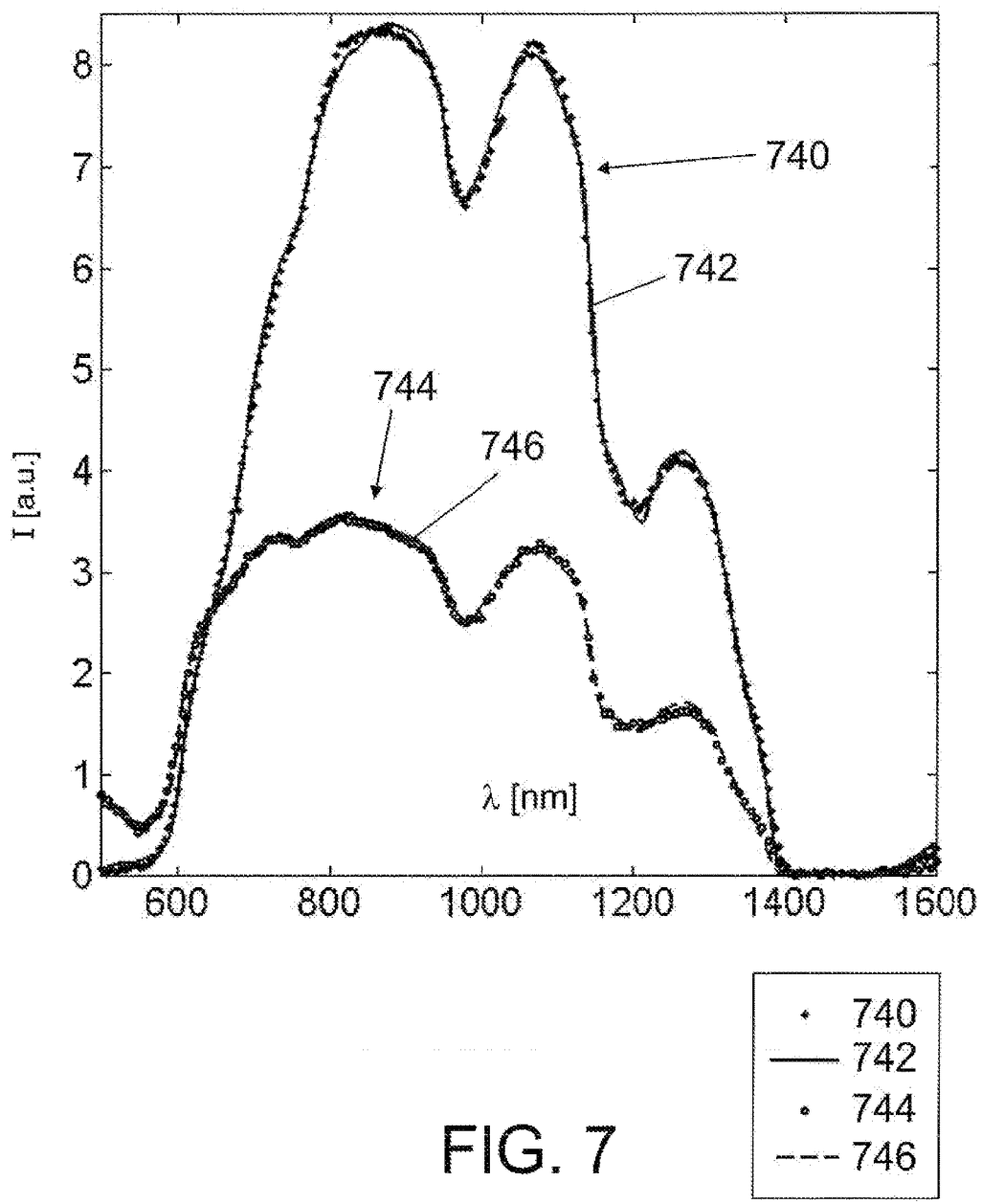
FIG. 7 shows reflectance measurement from normal and cancerous site and their corresponding fits.

FIG. 7 shows a graph with reflectance measurements 740 from normal site and a corresponding fit 742. The reflectance measurement from the normal site and corresponding fit is shown in the upper part of the graph. FIG. 7 furthermore shows a graph with reflectance measurements 744 from a cancerous site and a corresponding fit 746. The reflectance measurement from the cancerous site and corresponding fit is shown in the lower part of the graph. FIG. 7 shows a typical spectrum from both healthy and metastatic liver tissues with their corresponding fit curves. Major differences between the two typical spectra showed a difference in the estimated parameters. The graph has on its first, horizontal axis, the wavelength (λ, lambda) given in nanometer (nm), and on its second, vertical axis, the intensity (I) given in arbitrary units (a.u.).

For diffuse reflectance, an algorithm has been developed that can be used to derive optical tissue properties such as the scattering coefficient and absorption coefficient of different tissue chromophores: e.g. haemoglobin, oxygenated haemoglobin, water, lipid, collagen and elastin from the diffuse reflectance spectra. These properties may be different between normal and pathology tissues. In more detail the algorithm can be described as follows. The spectral fitting will be performed by making use of the analytically derived formula for reflectance spectroscopy (see Nachabé2010). This reflectance distribution R is given by $$R(\rho) = \int_0^\infty R(\rho, z_0) \delta\left(z_0 - \frac{1}{\mu_t'}\right) dz_0 \qquad (1a)$$

$$= \frac{a'}{4\pi} \left[ \frac{\frac{1}{\mu_t'}\left(\mu_{\mathit{eff}} + \frac{1}{\tilde{r}_1}\right)\frac{e^{-\mu_{\mathit{eff}} \tilde{r}_1}}{\tilde{r}_1^2} + }{\left(\frac{1}{\mu_t'} + 2z_b\right)\left(\mu_{\mathit{eff}} + \frac{1}{\tilde{r}_2}\right)\frac{e^{-\mu_{\mathit{eff}} \tilde{r}_2}}{\tilde{r}_2^2}} \right]$$

-continued where $$\tilde{r}_1 = \sqrt{x^2 + y^2 + \left(\frac{1}{\mu'_t}\right)^2}$$

$$\tilde{r}_2 = \sqrt{x^2 + y^2 + \left(\frac{1}{\mu'_t} + 2z_b\right)^2}$$

$$\mu_{eff} = \sqrt{3\mu_a[\mu_a + \mu_s(1-g)]}$$

In this formula the three macroscopic parameters describing the probability of interaction with tissue are: the absorption coefficient $\mu_a$ (mu_a) and the scattering coefficient $\mu_s$ (mu_s) both in reciprocal centimeters (cm$^{-1}$) as well as by g which is the mean cosine of the scattering angle. Furthermore, we have the total reduced attenuation coefficient $\mu'_t$ (mu_t') that gives the total chance for interaction with tissue $$\mu'_t = \mu_a + \mu_s(1-g) \tag{2a}$$

The albedo a' is the probability of scattering relative to the total probability of interaction $$a' = \mu_s/\mu'_t \tag{3a}$$

We assume a point source at a depth $z_0 = 1/\mu'_t$ and no boundary mismatch hence $z_b = 2/(3\mu'_t)$. Furthermore, we assume that the scattering coefficient can be written as $$\mu'_s(\lambda) = a\lambda^{-b} \tag{4a}$$

The main absorbing constituents in normal tissue dominating the absorption in the visible and near-infrared range are blood (i.e. haemoglobin), water and lipids. Myoglobins may also be present in significant concentrations in muscle tissue. In FIG. 3 the absorption coefficient of these chromophores as a function of the wavelength are presented. Note that blood dominates the absorption in the visible range, while water and lipids dominate in the near infrared range. When a bile containing structure is present the spectra will as well be influenced by bile.

The total absorption coefficient is a linear combination of the absorption coefficients of blood, water, lipid and bile (hence for each component the value of that shown in FIG. 3 and FIG. 4 multiplied by its volume fraction). By fitting the above formula while using the power law for scattering we can determine the volume fractions of the blood, water, lipid and bile as well as the scattering coefficient. With this method we can translate the measured spectra in physiological parameters that can be used to discriminate different tissue types, such as tissue structures, within the liver organ. As can be observed in FIGS. 5-6 the effect of bile on the diffuse reflectance spectrum can be significantly dependent on the concentration of bile.

Another method for deriving optical properties from diffuse reflectance spectra is to utilize look-up tables that have been created with a library of phantoms. The reference Rajaram N, Nguyen T H, Tunnell J W., "Lookup table-based inverse model for determining the optical properties of turbid media," Journal of Biomedical Optics 13(5):050501, 2008, describes this approach and is hereby incorporated by reference.

Another way to discriminate differences in spectra is by making use of multivariate statistical analysis methods such as principal component analysis, and partial least squares discriminant analysis which render classification of differences in spectra and thus allows discrimination between tissues.

Figure 8:
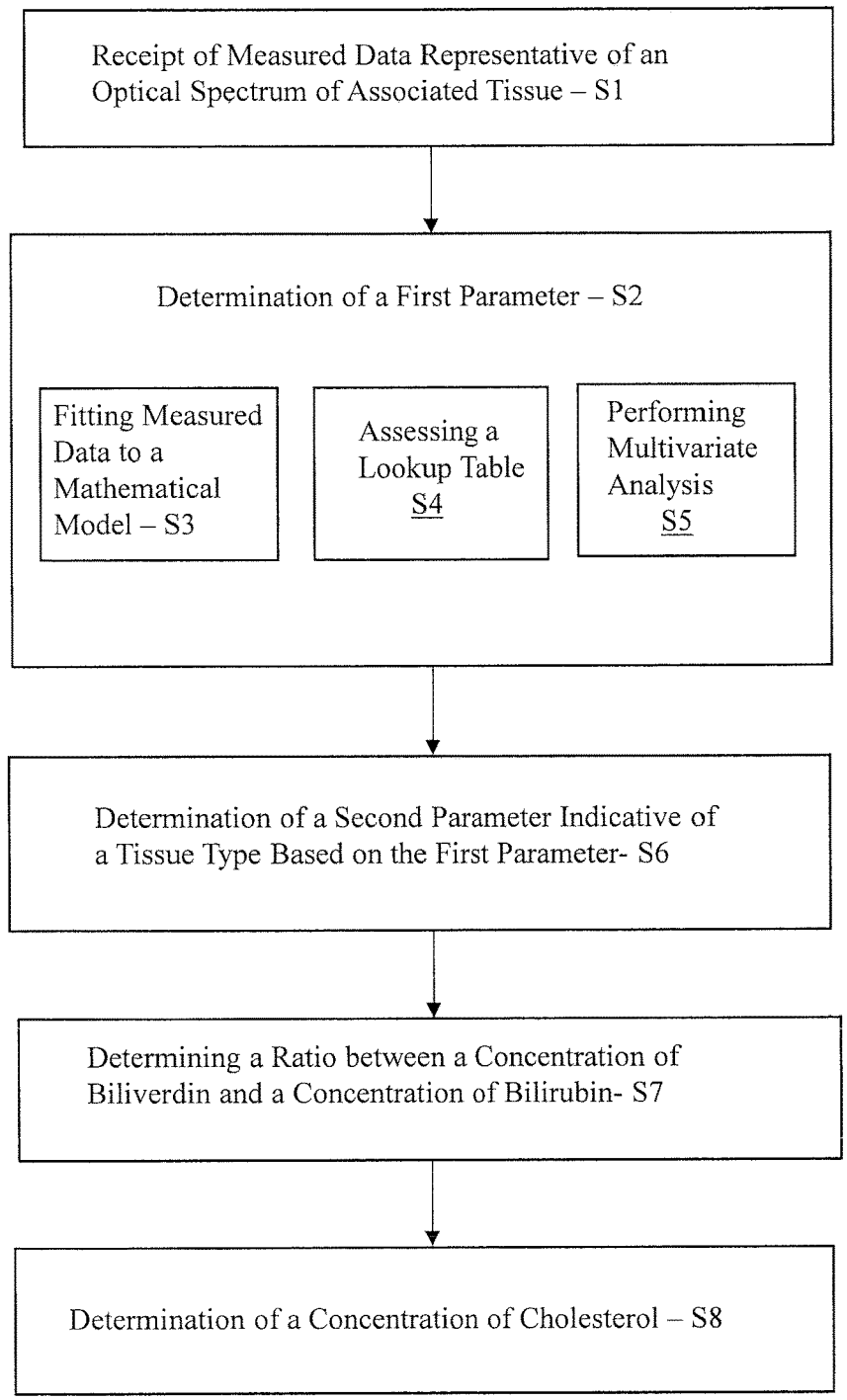
FIG. 8 is a flow-chart of a method according to the invention.

FIG. 8 is a flow chart of a method according to an embodiment of the invention comprising the steps of receipt S1 of measured data representative of an optical spectrum of the associated tissue, determination S2 of a first parameter, the first parameter being indicative of a concentration of bile, based on the measured data, wherein the determination of the first parameter includes any one of: fitting the measured data to a mathematical model S3, assessing a look-up-table S4 comprising predetermined optical spectra, and performing multivariate analysis S5. The method further comprising determination S6 of a second parameter based on the first parameter, the second parameter being indicative of a tissue type. The method further including the step of determination S7 of a ratio between a concentration of biliverdin and a concentration of bilirubin, and determination S8 of a concentration of cholesterol.

EXAMPLE

Patients and Liver Tissue Handling

An ex vivo study was conducted at the Netherlands Cancer Institute (Nederlands Kanker Instituut) under approval from the internal review board committee. Spectra were collected from liver surgical specimens after partial liver hepatectomy. The samples were sent from the surgery room to the pathology department. Before further processing of the samples was done (i.e. before fixation in formalin), the spectra on normal and tumor tissue were collected. In order to ensure that the measurements were at the tumor location the samples were cut by the pathologist such that the tumor was exposed. At the measurement sites tissue was collected for conventional histopathology. The slides were analyzed by well trained pathologists. The pathological findings were correlated with the optical measurements.

Several spectra were measured on liver tissues from 14 enrolled patients. In average, 15 spectra were taken from each of the fourteen healthy and metastatic liver tumor sites, respectively.

Instrumentation and Calibration

The spectra were collected from the different samples using the instrument that was previously described (Nachabé2010). Briefly, the setup consists of a halogen broadband light source with an embedded shutter, an optical probe with three fibers and two spectrometers that can resolve light from 400 to 1100 nm and 800 to 1700 nm, respectively. A filter that rejects light for wavelength below 465 nm was mounted in front of the spectrometers to reject second order light at the detectors. The probe has a fiber connected to the light source and the other fibers connected to the two spectrometers. The center-to-center distance separation between the emitting and collecting fibers is 2.48 mm. All optical fibers are low-OH fibers of 200 microns core diameter. The spectrometers are controlled by software to acquire the measured data.

The calibration consists of several steps. First, the detectors were cooled down to a temperature of −40° C. Once the temperature stabilized, a wavelength calibration was performed to assign a wavelength value to each pixel of both detectors, by fitting a second order polynomial to a set of atomic lines from argon and mercury light sources with peaks at known wavelengths. The following steps consisted of calibrating the system with a white reflectance standard measurement to compensate for the spectral shape of the light emitted by the lamp and the wavelength-dependent sensitivity of the detectors. This calibration step was followed by a background measurement. Each acquired spectrum was done by measuring simultaneously with both spectrometers.

Mathematical Modeling

The measured diffuse optical spectra were fit using the model of Farrell et al. (T. J. Farrel, M. S. Patterson and B. C. Wilson, "A diffusion theory model of spatially resolved, steady-state diffuse reflectance for the non-invasive determination of tissue optical properties," Med. Phys. 19 (1992) p. 879-888, which is hereby incorporated by reference) where the reduced scattering coefficient $\mu'_s(\lambda)$, the absorption coefficient $\mu_a(\lambda)$ and the center-to-center distance between the fibers at the tip of the probe are input arguments for the model. The spectra were fitted over the wavelength range of 500-1600 nm using a non-constrained linear least squares fitting algorithm.

The wavelength dependant reduced scattering coefficient is expressed with a double power law $$\mu'_s = a\left(\rho_{MR}\left(\frac{\lambda}{\lambda_0}\right)^{-b} + (1-\rho_{MR})\left(\frac{\lambda}{\lambda_0}\right)^{-4}\right) [\text{cm}^{-1}] \quad (1)$$

where the wavelength $\lambda$ is expressed in nm and is normalized to a wavelength value of 800 nm, $\lambda_0$. The reduced scattering coefficient is expressed as the sum of a Mie and a Rayleigh scattering where $\rho_{MR}$ is the Mie-to-Rayleigh reduced scattering fraction and b corresponds to the slope of the Mie reduced scattering. The total reduced scattering amplitude at $\lambda_0$ is denoted a.

We adopted the formulation of the absorption coefficient that is described earlier (Nachabé2010) where the absorption due to blood is expressed as $$\mu_a^{Tissue}(\lambda) = \mu_a^{Blood}(\lambda) + \mu_a^{WL}(\lambda) [\text{cm}^{-1}] \quad (2)$$

where $\mu_a^{Blood}(\lambda)$ corresponds to the absorption by blood and $\mu_a^{WL}$ corresponds to absorption by water and lipid in the probed tissue. The blood related absorption coefficient is given by $$\mu_a^{Blood}(\lambda) = C(\lambda)\nu_{Blood}[S_tO_2\mu_a^{HbO_2}(\lambda) + (1-S_tO_2)\mu_a^{Hb}(\lambda)][\text{cm}^{-1}] \quad (3)$$

where $\mu_a^{HbO_2}$ and $\mu_a^{Hb}$ are the absorption coefficient of oxygenated haemoglobin HbO₂ and deoxygenated haemoglobin Hb, respectively. The parameter $\nu_{Blood}$ corresponds to the blood volume fraction for a concentration of haemoglobin in whole blood of 150 mg/mL and $S_tO_2$ corresponds to the oxygen saturation of the blood in the probed volume. The factor C is a wavelength dependant correction factor known as a vessel packaging factor and is given by $$C(\lambda) = \frac{1 - \exp(-2R[S_tO_2\mu_a^{HbO_2}(\lambda) + (1-S_tO_2)\mu_a^{Hb}(\lambda)])}{2R[S_tO_2\mu_a^{HbO_2}(\lambda) + (1-S_tO_2)\mu_a^{Hb}(\lambda)]} \quad (4)$$

with R is the average vessel radius expressed in cm however its value will be reported in microns throughout this paper. The absorption due to the presence of water and lipid in the measured tissue is defined as $$\mu_a^{WL}(\lambda) = \nu_{WL}[\alpha\mu_a^{Lipid}(\lambda) + (1-\alpha)\mu_a^{H_2O}(\lambda)][\text{cm}^{-1}] \quad (5)$$

with $\mu_a^{H_2O}(\lambda)$ and $\mu_a^{Lipid}(\lambda)$ being the absorption coefficient of water and lipid respectively. The parameters $\nu_{WL}$ and $\alpha$ corresponds to the total volume fraction of water and lipid in the tissue and the lipid fraction within this volume, respectively. The advantage of describing the absorption due to water and lipid as described in equation (5) instead of the sum of absorption of water and lipid separately weighted by the corresponding volume fractions is that the covariance between $\nu_{WL}$ and $\alpha$ is smaller than between the volume fractions of water and lipid (see reference "Estimation of biological chromophores using diffuse optical spectroscopy: benefit of extending the UV-VIS wavelength range to include 1000 to 1600 nm" by Rami Nachabé, Benno H. W. Hendriks, Marjolein van der Voort, Adrien E. Desjardins, and Henricus J. C. M. Sterenborg, in Biomedical Optics Express, Vol. 1, Issue 5, pp. 1432-1442 (2010), which is hereby incorporated by reference). However, throughout this Example $\nu_{WL}$ and $\alpha$ are then converted to water and lipid fractions and reported as such because of their clinical relevance.

Absorption from bile was considered by incorporating its contribution into equation (2) so that the total absorption is expressed $$\mu_a^{Total}(\lambda) = \mu_a^{Tissue}(\lambda) + \nu_{Bile}\mu_a^{Bile}(\lambda)[\text{cm}^{-1}] \quad (6)$$

where $\nu_{Bile}$ and $\mu_a^{Bile}(\lambda)$ are the volume fraction and absorption coefficient of bile, respectively. The absorption coefficient was obtained by measuring fresh bile from a patient who underwent a cholecystectomy. The bile was poured in cuvettes of different thickness and the optical transmission was measured in a spectrophotograph (Lambda 900 Spectrometer, Perkin Elmer) with a resolution of 1 nm. FIG. 4 shows the absorption coefficient of bile, oxygenated and deoxygenated haemoglobin. Bile has a local absorption maximum at 600 nm and another local maxima below 500 nm.

From the acquired spectra the following parameters: a, b, $\rho_{MR}$, R, $\nu_{Blood}$, $S_tO_2$, $\nu_{WL}$, $\alpha$ and $\nu_{Bile}$ are determined. For each of these fit parameters, the confidence intervals were computed from the square root of the diagonal of the covariance matrix for a critical value of 0.05. Statistical F-test was performed to evaluate the improvement when bile is added to the model. The F-test is based on analyzing the difference between the sum-of-squares of the model with and without the bile absorption component. From the number of measured data points over the wavelength range where the fit is performed and the number of fit parameters for the models with and without the bile component, an F-ratio is computed from which a p-value can be extracted. If the p-value is smaller than a specific significance level (typically of 0.05), the model with the bile component leads to a better description of the measured spectra. Statistical comparison of the parameters estimated from the normal and tumor measurements was performed using the Kruskal Wallis non parametric test with significance determined by computed p-values.

Results

Mathematical Model Applied to the Healthy Liver Measurements

FIG. 5 shows a spectrum from 500 to 1600 nm of a normal liver sample (dotted curve 534), the corresponding fit curve without adding the bile component to the model (full line 536) and the 95% confidence bounds (dashed curves 538). The parameters obtained from the model are $\nu_{Blood}$=4.4±0.3%, $S_tO_2$=22±8%, R=76±13 μm, $\nu_{WL}$=91±2%, $\alpha$=17±2%, and a reduced scattering amplitude of 14.2±0.3 cm⁻¹ at 800 nm with a Mie to Rayleigh fraction of 19±4%. When investigating the residual and the confidence bounds, a large deviation between the measurement and the fit curves was observed around the deoxygenated haemoglobin peak at 758 nm.

Adding bile to the model, the large deviation around 758 nm significantly reduces while the confidence bounds narrowed between 500 and 1000 nm. Estimated values of $\nu_{Bile}$=3.9±0.7%, $\nu_{Blood}$=3.5±0.3%, $S_tO_2$=37±8%, R=56±13

µm, $v_{WL}$=93±2%, α=19±1%, and a reduced scattering amplitude of 14.5±0.3 cm$^{-1}$ at 800 nm with a Mie to Rayleigh fraction of 25±7% are found. In comparison to the outcome of the model without bile, the oxygen saturation level is higher indicating that the bile absorption was compensated by deoxygenated haemoglobin. The same observation can be deduced from the results of Table I that compares the average and standard deviation of the parameters obtained from all the spectra measured on the 14 normal human liver tissue samples.

In order to evaluate whether adding the bile absorption coefficient to the model does indeed correspond to the missing absorber, a statistical F-test was applied to all the measured data acquired at healthy sites in the liver. From the F-ratios it is possible to draw a conclusion whether adding the bile component improves the fitting procedure or not. If the F-ratios are close to unity then the model without bile is the best model however if they are greater than unity there are two possibilities. Either the model with bile is the best model that describes the measured data or the model with bile is the best however noise in the measurements lead the model with bile to smaller residuals. In order to know which one of both models describes best the measured data, the p-values are computed from the F-ratios. In total, 95% of the measured data have shown that the model with bile described best the measured spectra with a p-value below 0.05.

Comparison of the Measured Data Set of Healthy and Cancerous Tissue

FIG. 7 shows a typical spectrum from both healthy and metastatic liver tissues with the corresponding fit curves. Major differences between the two typical spectra showed a difference in the estimated parameters. From the typical metastatic tissue measurement depicted in FIG. 7, the estimated parameters and the corresponding confidence intervals are $v_{Bile}$=0±0%, $v_{Blood}$=1.5±0.1%, $S_rO_2$±3±5%, R=31±3 µm, $v_{WL}$=101±2%, α=10±1%, and a reduced scattering amplitude of 9.8±0.3 cm$^{-1}$ at 800 nm with a Mie to Rayleigh fraction of 76±4%.

Table I annexed to the description (ANNEX 1) shows the fit results for normal liver tissue with bile taken into account. The measured data originates from the measured diffuse reflectance spectra measured on normal liver tissue for 14 different human liver samples. The parameter S800 in Table I and Table II represents the total reduced scattering amplitude at $\lambda_0$=800 nm.

Table II annexed to the description (ANNEX 2) shows the fit results for tumor liver tissue with bile taken into account. The measured data originates from the measured diffuse reflectance spectra measured on tumor liver tissue with the same sample for 14 different human liver samples.

In terms of the experimental procedure, 14 liver samples were procured. Each liver sample contained a tumor (i.e. there was a part that still was normal tissue and a part being tumor tissue). In the normal part several measurements were made and in the tumor part several measurements were made. In Table I and Table II the averaged values obtained from these measurements in normal tissue and the averaged values obtained from these measurements in tumor tissue are presented, respectively. This was repeated for 14 patients.

Table III annexed to the description (ANNEX 3) shows averaged fit results for the normal and tumor liver tissue samples with bile taken into account. Notice particularly the last column, where it is evident that a significant difference in concentration of bile in terms of vol % is given for normal and tumor samples. The reduced scattering amplitude and the bile volume fraction showed the most significant differences (p<0.0001) between normal and metastatic liver tissues making them as the main two discriminators. This observation is consistent with the fact that the tumors in liver are metastasis of colon cancer with different structural composition. Normal liver tissue is mainly constituted of hepatocytes which are cells that are arranged as very thin plates separated by fine vascular sinusoids where blood flows and allowing perfusion of the bile throughout the liver. In the tumor this structure is lost, apparently causing a different perfusion of the bile as well as altered light scattering.

In Table I and Table II the fit results for normal and tumor liver tissue has been listed where bile is taken into account. In Table III the averaged fit results for the normal and tumor liver tissue samples with bile taken into account is listed. From these tables we can deduce that the bile concentration can be used as an additional parameter to distinguish different structures within the liver organ. In this case the bile concentration in tumor tissue is clearly lower than in normal liver tissue as can be deduced from the Kruskal Wallis statistical test indicated in Table III.

To sum up, the present invention relates to an apparatus 100 and, a method and a computer program for determining a parameter indicative of a tissue type of an associated tissue 116. In particular, the invention relates to an apparatus 100 comprising a spectrometer 102, which spectrometer comprises a light source 104 and a detector 106, 108 arranged to measure an optical spectrum. This enables determination of a first parameter being indicative of a bile concentration. As the inventors of the present invention have made the insight that bile concentration may serve as a discriminative feature for different tissue types, the apparatus is arranged to determine a second parameter indicative of a tissue type based on a concentration of bile. According to a specific embodiment, the apparatus further comprises an interventional device 112.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

Annex 1:

TABLE I

| Patient | Blood (%) | S800 (cm$^{-1}$) | R (microns) | Bile (%) | Mie/Ray |
|---|---|---|---|---|---|
| 1 | 3.89 | 19.30 | 87.39 | 15.34 | 0.17 |
| 2 | 2.38 | 22.87 | 58.22 | 2.85 | 0.41 |
| 3 | 0.99 | 20.77 | 16.84 | 5.71 | 0.06 |
| 4 | 4.28 | 16.14 | 60.30 | 5.41 | 0.49 |
| 5 | 2.86 | 16.19 | 51.34 | 9.87 | 0.59 |
| 6 | 2.02 | 14.86 | 32.70 | 3.51 | 0.42 |
| 7 | 3.24 | 18.96 | 54.12 | 6.48 | 0.62 |
| 8 | 5.67 | 16.61 | 75.02 | 3.32 | 0.52 |
| 9 | 4.15 | 12.21 | 45.33 | 2.16 | 0.51 |
| 10 | 0.94 | 18.39 | 8.86 | 18.04 | 0.10 |

TABLE I-continued

| Patient | Blood (%) | S800 (cm⁻¹) | R (microns) | Bile (%) | Mie/Ray |
|---|---|---|---|---|---|
| 11 | 3.15 | 14.19 | 30.37 | 5.51 | 0.54 |
| 12 | 3.42 | 14.94 | 55.34 | 6.09 | 0.20 |
| 13 | 1.92 | 18.56 | 44.07 | 4.50 | 0.17 |
| 14 | 9.15 | 19.13 | 78.83 | 3.39 | 0.46 |

Annex 2:

TABLE II

| Patient | Blood (%) | S800 (cm⁻¹) | R (microns) | Bile (%) | Mie/Ray |
|---|---|---|---|---|---|
| 1 | 6.24 | 13.82 | 549.96 | 1.12 | 0.12 |
| 2 | 0.98 | 13.82 | 55.56 | 0.39 | 0.69 |
| 3 | 0.69 | 9.48 | 104.78 | 1.54 | 0.47 |
| 4 | 11.62 | 11.55 | 79.27 | 3.28 | 0.74 |
| 5 | 0.48 | 10.63 | 18.82 | 0.81 | 0.60 |
| 6 | 0.28 | 7.85 | 20.37 | 0.12 | 0.57 |
| 7 | 3.66 | 9.02 | 47.38 | 2.87 | 0.62 |
| 8 | 0.56 | 3.27 | 602.55 | 1.55 | 0.89 |
| 9 | 1.19 | 7.98 | 49.05 | 0.60 | 0.57 |
| 10 | 0.42 | 12.07 | 34.13 | 0.41 | 0.54 |
| 11 | 0.68 | 14.18 | 11.82 | 3.77 | 0.34 |
| 12 | 0.04 | 5.32 | 92.10 | 0.73 | 0.67 |
| 13 | 9.51 | 10.18 | 640.67 | 1.92 | 0.11 |
| 14 | 1.21 | 8.13 | 144.80 | 0.05 | 0.48 |

Annex 3:

TABLE III

| Parameter | Normal (N = 14) | Metastatic (N = 14) |
|---|---|---|
| Bile (%)[a] | 6.6 ± 4.5 | 1.4 ± 1.1 |
| Blood volume fraction (%) | 3.4 ± 2.0 | 2.7 ± 3.6 |
| Blood oxygenation level (%)[a] | 8 ± 14 | 49 ± 38 |
| Average vessel radius (microns) | 50 ± 22 | 175 ± 224 |
| Water volume fraction (%)[a] | 76 ± 7 | 93 ± 17 |
| Lipid volume fraction (%) | 19 ± 11 | 12 ± 6 |
| Reduced scattering at 800 nm (cm⁻¹)[a] | 17 ± 3 | 10 ± 3 |
| Mie Slope | 1.0 ± 0.5 | 0.6 ± 0.4 |
| Mie to Rayleigh scattering fraction (%) | 37 ± 19 | 53 ± 21 |

[a]Indicates significant differences with $p < 0.01$ for the Kruskal Wallis test.

The invention claimed is:

1. An apparatus for optical analysis of an associated non-fluid tissue of an organ of a subject, the apparatus comprising:
    a spectrometer for obtaining measured data representative of an optical spectrum of the associated non-fluid tissue of the organ of the subject, the spectrometer comprising
    a light source,
    an optical detector,
    a processor, and
    a database, which database is operably connected to the processor, wherein the database comprises predetermined data representative of an optical spectrum of human bile,
    wherein the processor is arranged for
        receiving the measured data,
        determining from the measured data and the predetermined data representative of an optical spectrum of human bile a first parameter being indicative of a concentration of bile in said associated non-fluid tissue of the organ of the subject, and
        determining from the first parameter a second parameter being indicative of a tissue type for the associated non-fluid tissue of the organ of the subject.

2. An apparatus according to claim 1, wherein the processor is further arranged for determining a scattering parameter based on the measured data.

3. An apparatus according to claim 1, further comprising an interventional device, the interventional device comprising
    a first guide for guiding photons from the light source to an exit position on a distal end of the interventional device, the photons being emittable from the exit position, and
    a second guide for guiding photons from an entry position on the distal end of the interventional device and to the optical detector.

4. An apparatus according to claim 3, wherein the exit position and the entry position are spatially separated and spatially oriented so that, upon positioning the distal end of the interventional device adjacent to the associated tissue, an average spectral information of a region of the associated non-fluid tissue is obtainable from photons collectable at the entry position.

5. An apparatus according to claim 3, wherein the photons exiting the second guide are non-focused.

6. An apparatus according to claim 1, wherein the apparatus further comprises any one of: a second light source for providing therapeutic light and/or an ultrasound unit.

7. An apparatus according to claim 1, wherein the second parameter indicative of tissue type enables discrimination between tissue conditions.

8. An apparatus according to claim 1, wherein the second parameter indicative of tissue type enables discrimination between dysplastic tissue and normal tissue.

9. An apparatus according to claim 1, wherein the second parameter indicative of tissue type enables discrimination between normal tissue and tumor tissue.

10. A method for optical analysis of an associated non-fluid tissue of an organ of a subject, the method comprising the steps of:
    receipt of measured data representative of an optical spectrum of the associated non-fluid tissue of the organ of the subject,
    determination of a first parameter, the first parameter being indicative of a concentration of bile, based on the measured data and predetermined data representative of an optical spectrum of human bile, and
    determination of a second parameter based on the first parameter, the second parameter being indicative of a tissue type for the associated non-fluid tissue of the organ of the subject.

11. A method according to claim 10 for optical analysis of an associated tissue, wherein the determination of the first parameter includes fitting the measured data to a mathematical model.

12. A method according to claim 10 for optical analysis of an associated non-fluid tissue, wherein the determination of the first parameter includes any one of:
    assessing a look-up-table comprising predetermined optical spectra, and
    performing multivariate analysis.

13. A method according to claim 10 for optical analysis of an associated non-fluid tissue, the method further including the step of:
    determination of a ratio between a concentration of biliverdin and a concentration of bilirubin.

14. A method according to claim 10 for optical analysis of an associated non-fluid tissue, the method further comprising the step of:
    determination of a concentration of cholesterol.

15. A non-transitory computer readable medium storing a computer program product adapted to enable a computer to carry out the method of claim 10.

* * * * *